United States Patent [19]

Kompis

[11] Patent Number: 4,532,245

[45] Date of Patent: Jul. 30, 1985

[54] PHARMACEUTICAL COMPOSITIONS

[75] Inventor: Ivan Kompis, Oberwil, Switzerland

[73] Assignee: Hoffmann-La Roche Inc., Nutley, N.J.

[21] Appl. No.: 507,842

[22] Filed: Jun. 27, 1983

Related U.S. Application Data

[63] Continuation of Ser. No. 243,151, Mar. 12, 1981, abandoned.

[30] Foreign Application Priority Data

Mar. 25, 1980 [CH] Switzerland .......................... 2328/80

[51] Int. Cl.³ ............................................ A61K 31/625
[52] U.S. Cl. .................................................... 514/275
[58] Field of Search .......................... 424/229

[56] References Cited

FOREIGN PATENT DOCUMENTS

| | | |
|---|---|---|
| 0174151 | 3/1953 | Austria . |
| 0351166 | 12/1978 | Austria . |
| 2400218 | 1/1974 | Fed. Rep. of Germany . |
| 0544053 | 12/1973 | Switzerland . |
| 0792449 | 3/1958 | United Kingdom . |

*Primary Examiner*—Delbert R. Phillips
*Assistant Examiner*—F. Moezie
*Attorney, Agent, or Firm*—Jon S. Saxe; George M. Gould; John J. Maitner

[57] ABSTRACT

Pharmaceutical compositions of sulfonamide and sulfonamide-potentiator are disclosed. These compositions, which are suitable for injection administration, comprise an aldehyde in addition to the sulfonamide and its potentiator.

1 Claim, No Drawings

PHARMACEUTICAL COMPOSITIONS

This is a continuation of application Ser. No. 243,151 filed Mar. 12, 1981, now abandoned.

BACKGROUND OF THE INVENTION

Combinations of sulfonamides and sulfonamide-potentiators have long been known as antibacterials and have been used extensively for the treatment of bacterial infections in humans and in animals.

However, the sulfonamides and their potentiators have different solubility characteristics. Since a weak acid sulfonamide must be combined in non-stoichiometric amounts with a weak base potentiator, difficulties have been encountered in the preparation of useful pharmaceutically acceptable solutions (e.g., injectable solutions) made by combining these materials.

The solutions prepared by the procedures disclosed in the prior art have not been completely satisfactory. Problems such as solvent compatibility (especially where large quantities of organic solvents were used), precipitation of the active ingredients from the solutions, solution instabilities and processing costs hampered the development of compositions suitable for injection use.

It is an object of this invention, therefore, to provide pharmaceutical compositions, in aqueous form or in a composition readily convertible to aqueous form, which compositions have acceptable solvent compatibility, dissolve sufficiently high concentrations of active material, have physiologically acceptable pHs, are stable and require no expensive adjuvants.

SUMMARY OF THE INVENTION

The present invention is directed to aqueous pharmaceutical compositions, suitable for injection administration, which comprise a water-soluble sulfonamide salt, a sulfonamide-potentiator and an aldehyde. This invention is also directed to compositions comprising dry solid residue compositions of the sulfonamide, potentiator and aldehyde which can be converted to the above aqueous compositions by the addition of water.

DETAILED DESCRIPTION OF THE INVENTION

The aqueous pharmaceutical compositons, or dry residues thereof, which comprise sulfonamide, potentiator and aldehyde are not mere solutions of the three components in water. The fact that dry residues can be reconstituted to aqueous solutions as well as physico-chemical investigations indicate that a chemical entity may have been formed from a reaction, inter alia, of the aldehyde. For example, a composition prepared from formaldehyde, trimethoprim and sulfadoxine has two signals, at 67.51 and 52.74 ppm, in the $^{13}C$ nuclear resonance spectrum which are characteristic for methylene groups and no carbonyl band in the IR spectrum which is characteristic for formaldehyde.

Sulfonamides which are suitable for use in the pharmaceutical compositions of this invention are especially $N^1$-heterocyclic substituted sulfonamides such as those having a 5- or 6-membered heterocycle (e.g. a pyrimidine, pyrazine, pyridazine, oxazole, isoxazole, thiazole or thiadiazole ring). Specific examples of sulfonamides are sulfadiazine, sulfamethoxazole, sulfatroxazole, sulfamerazine, sulfadoxine, sulfadimethoxine, sulfamethazine, sulfapyrazole, sulfaquinoxaline, sulfachloropyridazine, sulfaguanidine, sulfalene, sulfametin, sulfamethoxine, sulfamethoxy-pyridazine, sulfamethylphenazole, sulfaphenazole, sulfamoxole, sulfapyrazine, sulfapyridazine, sulfapyridine, sulfasymazine, sulfathiozole and sulfametrole.

Sulfonamide-potentiators are compounds which, when used in combination with a sulfonamide, exhibit an increase in the antibacterial activity of the sulfonamide which is much more than additive. Such sulfonamide-potentiators include, especially, compounds which inhibit dihydrofolate reductase and, preferably, 2,4-diaminopyrimidine derivatives. Such 2,4-diaminopyrimidine derivatives include 2,4-diamino-5-benzyl-pyrimidines substituted in the phenyl ring such as 2,4-diamino-5-(3,4,5-trimethoxybenzyl)-pyrimidine (trimethoprim),2,4-diamino-5-[3,5-dimethoxy-4-(2-methoxyethoxy)benzyl]-pyrimidine (tetroxoprim) and 2,4-diamino-5-(3,5-dimethoxy-4-methylthiobenzyl)-pyrimidine (metioprim). Other dihydrofolate reductase inhibitors include 2,4-diamino-5-(4-bromo-3,5-dimethoxybenzyl)-pyrimidine, 2,4-diamino-5-[3,5-diethoxy-4-pyrrol-1-yl)-benzyl]-pyrimidine, 2,4-diamino-5-(3,4-dimethoxybenzyl)-pyrimidine (diaveridine),2,4-diamino-5-(p-chlorophenyl)-6-ethylpyrimidine (pyrimethanine) and 2,4-diamino-5-(2-methyl-4,5-dimethoxybenzyl)-pyrimidine.

Of particular interest as sulfonamide/sulfonamide-potentiator combinations of the pharmaceutical compositions of this invention are
sulfamethoxazole/trimethoprim;
sulfadiazine/trimethoprim;
sulfadoxine/trimethoprim;
sulfametrole/trimethoprim;
sulfadiazine/tetroxoprim and
sulfadoxine/pyrimethamine.

The aldehyde used for the preparation of the pharmaceutical compositions of this invention is preferably a lower aliphatic aldehyde and, especially, formaldehyde. Other aldehydes which can be used in the compositions are glycol aldehyde and glycerine aldehyde.

The molar ratio of sulfonamide-potentiator to aldehyde is conveniently equal to or less than 1 to 1 ($\leq 1:1$), that is, one or more mols of aldehyde per mol of potentiator. A preferred molar ratio of potentiator to aldehyde is 1:1 to 1:4 and, especially, the range of 1:1.5 to 1:2.5.

The amount of sulfonamide in the pharmaceutical compositions of this invention is, of course, determined by the therapeutic activity of the sulfonamide/sulfonamide-potentiator combinations. In the commercial combinations the molar ratio sulfonamide to potentiator is equal to or greater than 1 to 1 ($\geq 1:1$). that is, one or more moles of sulfonamide per mole of potentiator. In the case of the commercial composition of sulfamethoxazole: trimethoprim it is about 5.7:1 (corresponding to a weight ratio of 5:1). A preferred composition of this invention comprises sulfamethoxazole, trimethoprim and formaldehyde in the molar ratio of about 5.7:1:2.

The compositions of this invention can be prepared, as a general rule, by mixing the ingredients and warming the resulting mixture, conveniently at about 80° C. For example, a potentiator and aqueous aldehyde solution are added to an aqueous solution of a sulfonamide salt and the mixture is warmed until complete solution has occurred. The sulfonamide is conveniently dissolved in water containing the requisite amount of base for salt formation. In a particular embodiment, the aqueous aldehyde solution is added to the solution of the sulfonamide salt and the potentiator is then added.

Suitable bases for the sulfonamide salt formation are, especially, alkali hydroxides such as sodium hydroxide or potassium hydroxide or pharmaceutically acceptable organic bases such as N-methylglucamine or basic amino acids such as lysine, arginine or ornithine.

The concentration of dissolved materials in the solution compositions of this invention can be 40 percent by weight or more with 10 to 20 percent by weight solutions preferred.

For certain sulfonamide-potentiator combinations, a suitable organic solvent which is miscible with water, such as glycofurol or polyethyleneglycol 400, can be added to the solution during the preparation.

The aqueous compositions of this invention can be dried using galenical techniques known per se as, for example, freeze-drying or spray-drying. The resulting dry compositions, which are also a part of this invention, can be reconverted, if desired, after sterilization, into solutions (e.g. injection solutions) by the addition of water.

The compositions of this invention can also be sterilized by means of galenical techniques which are usual in the preparation of parenteral administration forms as, for example, heat sterilization or sterile filtration.

The compositions of this invention can be used, in addition to use as injectable solutions, in other means of administration in which a sulfonamide/sulfonamide-potentiator combination in solution form should be used.

The compositions of this invention exhibit both in vitro and in vivo antibacterial activity of the corresponding and known sulfonamide/sulfonamide-potentiator combinations and can, therefore, be used for the same indications.

The following Examples illustrate this invention.

EXAMPLE 1

800 mg of sulfamethoxazole are dissolved under nitrogen in 3.15 ml of 1N sodium hydroxide at 40° C. The solution is then diluted with ca 5 ml of water. 160 mg of trimethoprim and 0.08 ml of ca 35% formaldehyde solution, or an equivalent amount of paraformaldehyde, are then added. The stirred suspension is immersed in a bath (warmed at 80° C.) for 5-7 minutes and a clear solution results. After the solution cools to room temperature, the volume is made up to 10 ml with water. The resulting solution has a pH of 8.8.

EXAMPLE 2

Following the procedure of Example 1, 800 mg of sulfamethoxazole, 3.15 ml of 1N sodium hydroxide, 160 mg of trimethoprim, 132 mg of glycol aldehyde and water (q.s. to 10 ml) are used to prepare a solution having a pH of 8.6.

EXAMPLE 3

Following the procedure of Example 1, 1.5 g of trimethoprim, 4.5 g of sulfadiazine, 18.0 ml of 1N sodium hydroxide, 0.9 ml of ca 35% formaldehyde solution and water (q.s. to 100 ml) are used to prepare a solution having a pH of 9.1.

EXAMPLE 4

Following the procedure of Example 1, 2.0 g of tetroxoprim, 5.0 of sulfadiazine, 20.0 ml of 1N sodium hydroxide, 0.85 ml of ca 35% formaldehyde solution and water (q.s. to 100 ml) are used to prepare a solution having a pH of 9.5.

EXAMPLE 5

Following the procedure of Example 1, 4.0 g of trimethoprim, 20.0 of sulfadoxine, 64.5 ml of 1N sodium hydroxide, 1.8 ml of ca 35% formaldehyde solution and water (q.s. to 100 ml) are used to prepare a solution having a pH of 9.1.

EXAMPLE 6

Following the procedure of Example 1, 4.0 g of trimethoprim, 20.0 g of sulfatroxazole, 74.8 ml of 1N sodium hydroxide, 1.5 ml of ca 35% formaldehyde solution and water (q.s. to 100 ml) are used to prepare a solution having a pH of 9.2.

EXAMPLE 7

Following the procedure of Example 1, 4.0 g of 2,4-diamino-5-(4-bromo-3,5-dimethoxy-benzyl)-pyrimidine, 20.0 g of sulfadimethoxine, 32.0 ml of 2N sodium hydroxide, 40.0 ml of glycofurol 75, 2.2 ml of ca 35% formaldehyde solution and water (q.s. to 100 ml) are used to prepare a solution having a pH of 9.6.

EXAMPLE 8

Following the procedure of Example 1, 1.6 g of trimethoprim, 8.0 g of sulfametrole, 28.0 ml of 1N sodium hydroxide, 0.8 ml of ca 35% formaldehyde solution and water (q.s. to 100 ml) are used to prepare a solution having a pH of 9.6.

EXAMPLE 9

Following the procedure of Example 1, 4.08 g of trimethoprim, 20.4 g of sulfadimethoxine, 66 ml of 1N sodium hydroxide, 2.5 ml of ca 35% formaldehyde solution and water (q.s. to 100 ml) are used to prepare a solution having a pH of 9.6.

EXAMPLE 10

Following the procedure of Example 1, 10.86 g of a molecular compound trimethoprim-sulfamethoxazole (1:1) [F. Giordano, J. P. Bettinetti, A. La Manca, P. Ferloni, II Pharmaco Ed Sci., 32, 889 (1977)], 20 ml of 1N sodium hydroxide, 1.3 g of paraformaldehyde (95-97%) and water (q.s. to 100 ml) are used to prepare a solution having a pH of 9.75. This solution was evaporated to dryness at 25° under reduced pressure (0.1 Torr) and the residue was dried at room temperature for 48 hours.

Analysis of the residue (2 analyses). Found: C 50.18%; H 5.29%; N 15.49%; S 4.98%; C 50,19%; H 5.16%; N 15,69%; S 5.09%. H$_2$O: 3.86%.

This residue can be dissolved in 100 ml of water to reconstitute an injectable solution.

EXAMPLE 11

Following the procedure of Example 1, 5 g of sulfadoxine, 16.1 ml of 1N sodium hydroxide, 0.25 of pyrimethamine and 0.80 ml of ca 35% formaldehyde solution with the addition of 7.5 ml of polyethyleneglycol 400 and water (q.s. to 50 ml) are used to prepare a solution having a pH of 9.1.

EXAMPLE 12

320 g of sulfamethoxazole are suspended under nitrogen in ca 1 liter of water and subsequently dissolved by the addition of 20% sodium hydroxide solution (ad pH 8.8). 32 ml of ca 35% formaldehyde solution are added to this solution and the mixture is then warmed to 90° C.

Thereafter, 64 g of trimethoprim are added and dissolved with stirring. The solution is cooled to room temperature, the pH of the solution is adjusted to 9.0 and the total volume is made up to 2 liters with water. This solution can be lyophilized at −32° C. (freezing temperature −35° C.).

I claim:

1. An aqueous pharmaceutical composition, suitable for injection use, which comprises a reaction product formed from a water-soluble antibacterial sulfonamide salt selected from the group consisting of sulfadiazine, sulfamethoxazole, sulfatroxazole, sulfamerazine, sulfadoxine, sulfadimethoxine, sulfamethazine, sulfapyrazole, sulfaquinoxaline, sulfachloropyridazine, sulfaguanidine, sulfalene, sulfametin, sulfamethoxine, sulfamethoxy-pyridazine, sulfamethylphenazole, sulfaphenazole, sulfamoxole, sulfapyrazine, sulfapyridazine, sulfapyridine, sulfasymazine, sulfathiozole and sulfametrole, a sulfonamide-potentiator selected from the group consisting of substituted 2,4-diamino-5-benzyl-pyrimidine derivatives and formaldehyde, wherein the molar ratio of sulfonamide to sulfonamide-potentiator is equal to or greater than 1 to 1 and the mole ratio of sulfonamide-potentiator to formaldehyde is equal to or less than 1 to 1, and wherein said reaction product is obtained by mixing an aqueous solution of the sulfonamide salt, the sulfonamide-potentiator and aqueous formaldehyde and warming the mixture until complete solution occurs.

* * * * *